US00PP36066P2

(12) United States Plant Patent
Roberts et al.

(10) Patent No.: US PP36,066 P2
(45) Date of Patent: Aug. 13, 2024

(54) ***VITEX* PLANT NAMED 'BAILTEXFOUR'**

(50) Latin Name: *Vitex agnus-castus*
Varietal Denomination: Bailtexfour

(71) Applicant: Bailey Nurseries Inc., Newport, MN (US)

(72) Inventors: David Jonathan Roberts, Athens, GA (US); Oren McBee, Bishop, GA (US); Justin Schulze, Athens, GA (US)

(73) Assignee: BAILEY NURSERIES INC, Newport, MN (US)

( * ) Notice: Subject to any disclaimer, the term of this patent is extended or adjusted under 35 U.S.C. 154(b) by 0 days.

(21) Appl. No.: 18/510,379

(22) Filed: Nov. 15, 2023

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Vitex* plant named 'Bailtexfour' that is characterized by its compact plant size; reaching 0.9 to 1.2 m in height and width, its early and reblooming flowering habit, its vigorous growth habit from a young plant, and its tight and rounded plant form.

3 Drawing Sheets

Botanical classification: *Vitex agnus-castus*.
Variety denomination: 'Bailtexfour'.

BACKGROUND OF THE INVENTION

The present invention relates to a new and distinct cultivar of *Vitex agnus-castus*. The new *Vitex* will hereafter be referred to by its cultivar name, 'Bailtexfour'. 'Bailtexfour' is a new cultivar of chaste tree grown for use as an ornamental landscape plant.

The new cultivar was derived from a controlled breeding program conducted by the Inventors in Watkinsville, Georgia. The goal of the breeding program is to develop new cultivars of *Vitex agnus-castus* with compact reblooming plant habits.

The new cultivar arose as a seedling in Watkinsville, Georgia from seeds planted from open pollination of unnamed and unpatented plants of *Vitex agnus-castus* in summer of 2017. The male parent is therefore unknown. The Inventors selected the new cultivar as a single unique plant in summer of 2018.

Asexual propagation of the new cultivar was first accomplished by softwood stem cuttings by one of the Inventors in Watkinsville, Georgia in summer of 2019. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. The attributes in combination distinguish 'Bailtexfour' as a unique cultivar of *Vitex*.

1. 'Bailtexfour' exhibits a compact plant size; reaching 0.9 to 1.2 m in height and width.
2. 'Bailtexfour' exhibits an early and reblooming flowering habit.

3. 'Bailtexfour' exhibits a vigorous growth habit from a young plant.
4. 'Bailtexfour' exhibits a tight and rounded plant form.

The female parent plant differs from 'Bailtexfour' in having a larger plant size and a more open habit and in lacking re-bloom habit. 'Bailtexfour' can be most closely compared to *Vitex* 'PIIVAC-II' (U.S. Plant Pat. No. 26,775) and 'Bailtexthree' (U.S. Plant Pat. No. 35,259). 'PIIVAC-II' is similar to 'Bailtexfour' in having light purple flowers, early flowering and re-blooming. 'PIIVAC-II' differs from 'Bailtexfour' in having a larger size plant size, a later flowering period with sparse re-blooming, flowers that are lighter purple in color, and a slower growth habit from a young plant. 'Bailtexthree' is similar to 'Bailtexfour' in having light purple flowers and a rounded plant shape. 'Bailtexthree' differs from 'Bailtexfour' in having a larger plant size, an earlier flower period, and foliage that is lighter green in color and less glossy.

BRIEF DESCRIPTION OF THE DRAWINGS

The accompanying color photographs illustrate the overall appearance and distinct characteristics of the new *Vitex*. The photographs were taken of 1.5-year-old plants of the new cultivar as grown outdoors in the ground in Cottage Grove, Minnesota.

The photograph in FIG. 1 provides a side view of 'Bailtexfour' in bloom.

Figure 1:
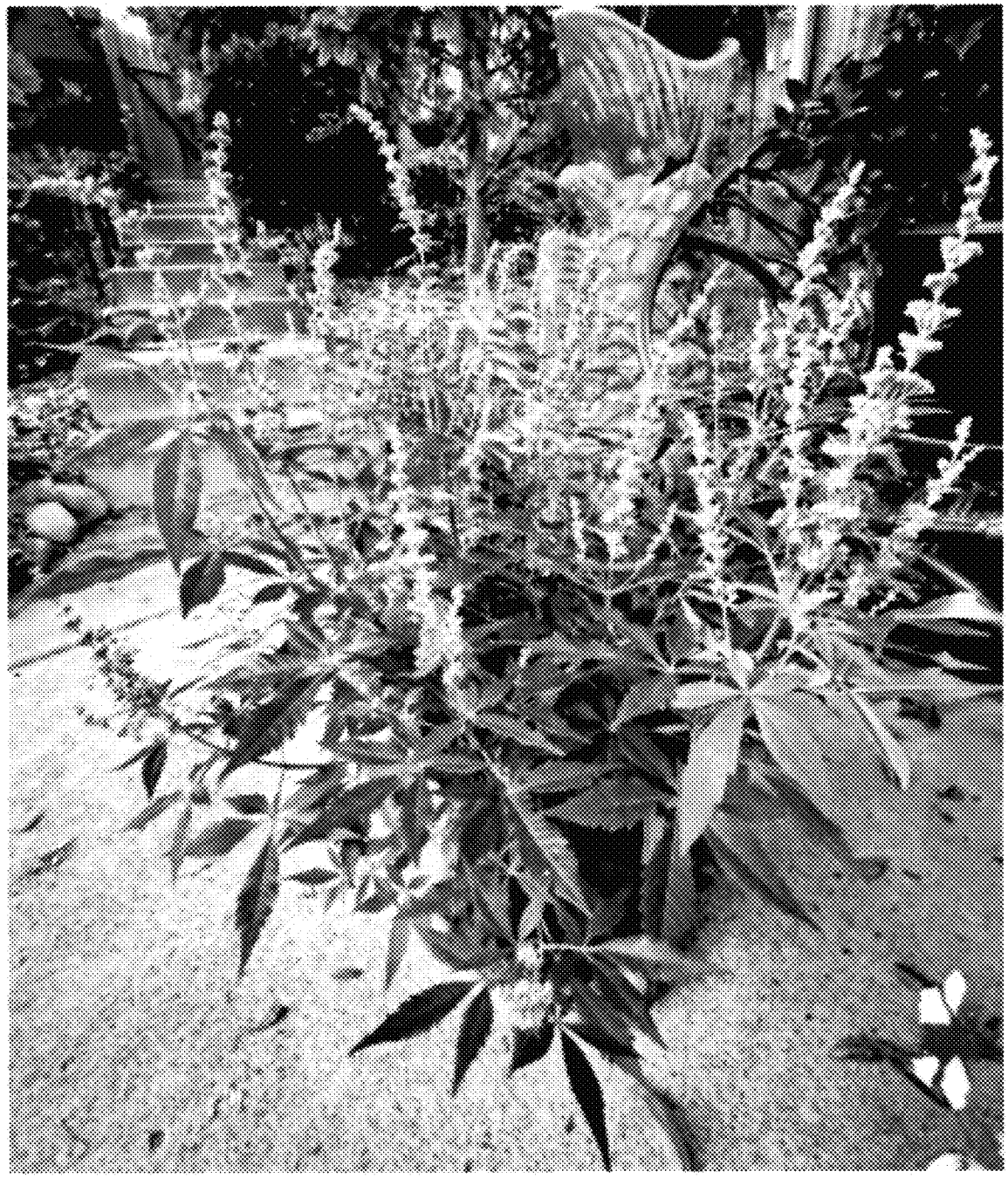
Figure 2:
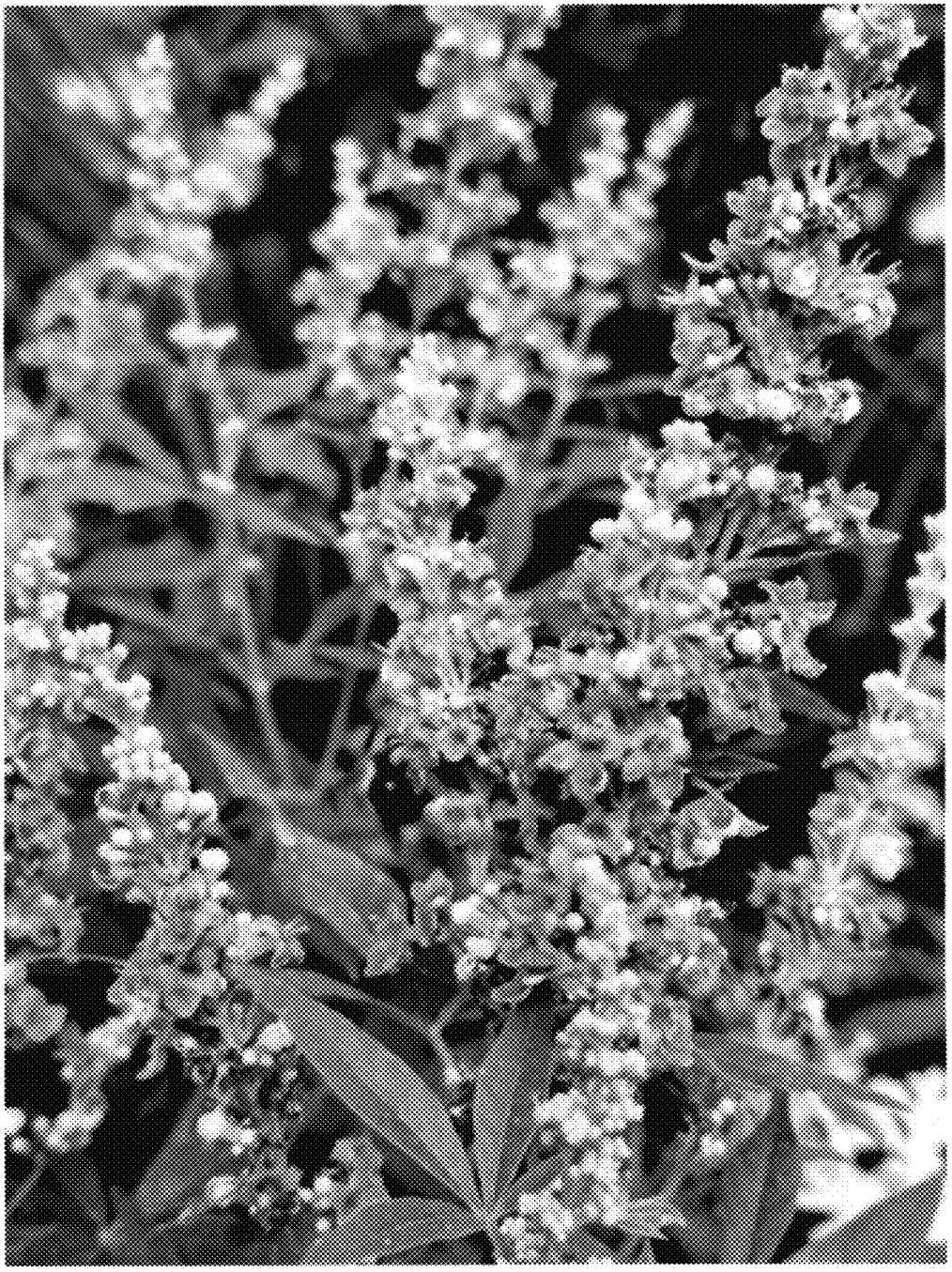

The photograph in FIG. 2 provides a close-up view of the inflorescences of 'Bailtexfour'.

Figure 3:
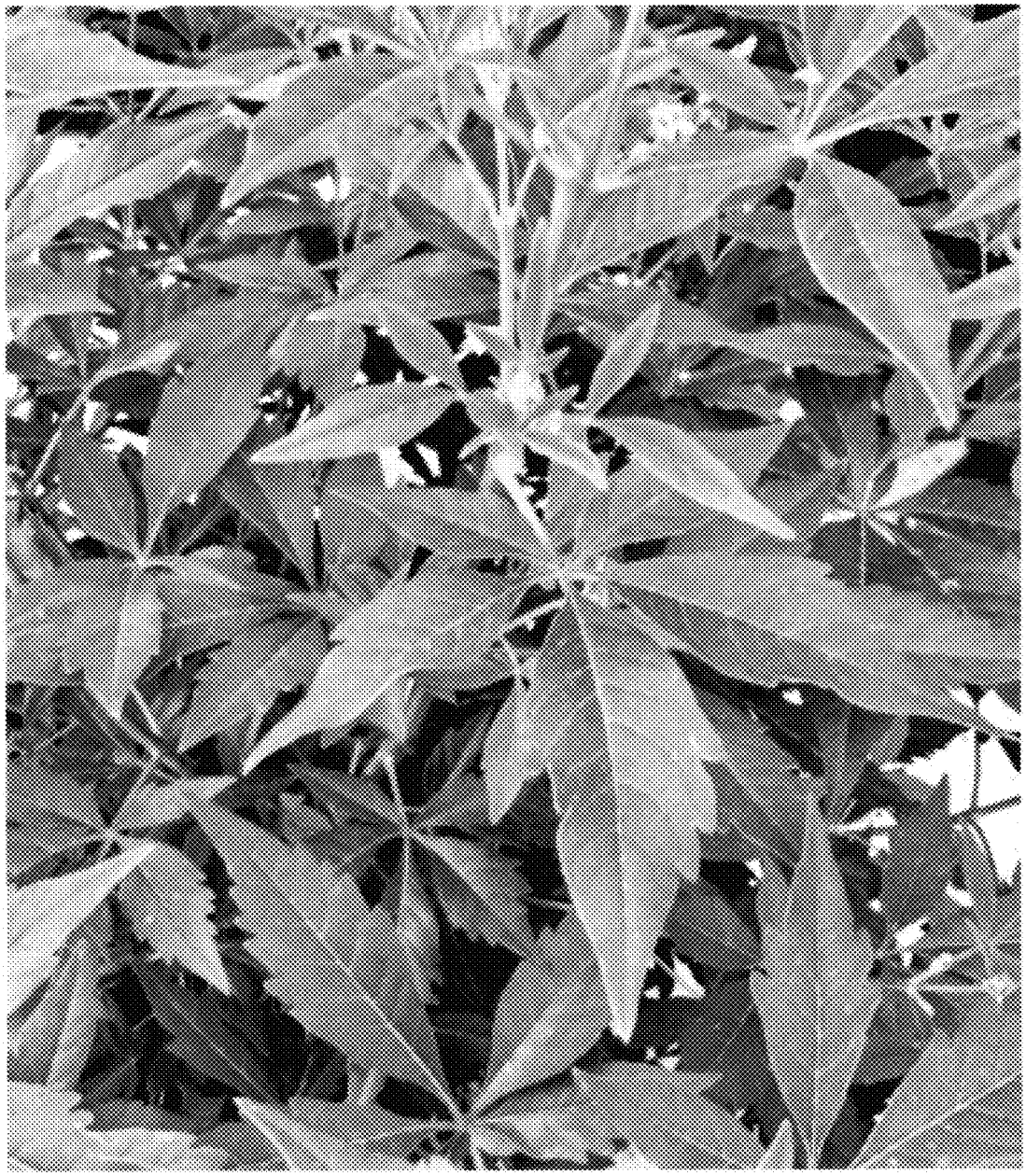

The photograph in FIG. 3 provides a close-up view of the foliage of 'Bailtexfour'.

The colors in the photographs are as close as possible with the photographic and printing technology utilized and the color values cited in the detailed botanical description accurately describe the colors of the new *Vitex*.

DETAILED BOTANICAL DESCRIPTION

The following is a detailed description of plants 1.5-year-old plants as grown in 2-gallon containers in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June and reblooming until frost in Winterville, Georgia.

*Plant type*.—Deciduous flowering shrub.

*Plant habit*.—Compact with a tight rounded form.

*Height and spread*.—An average of 42 cm in height and 63 cm in width as a 1.5-year-old plant in a container, 0.9 to 1.2 m in height and spread as a mature plant in the landscape.

*Cold hardiness*.—At last to U.S.D.A. Zone 5.

*Diseases and pests*.—No susceptibility or resistance to diseases or pests has been observed.

*Root description*.—156A in color, young roots are fibrous, older roots become woody.

*Propagation*.—Softwood stem cuttings.

*Root development*.—An average of 20 days for root initiation and an average of 60 days to produce a young rooted plant.

*Growth rate*.—Vigorous growth from a young plant.

Branch description:

*Branch strength*.—Strong.

*Branch length*.—Main; 13 cm in length, 8 mm in diameter, lateral; 26 cm in length (excluding peduncle), 4 mm in diameter.

*Branch quantity*.—Main; 2, lateral; 14 (7 pairs).

*Branch aspect*.—Upright to outward.

*Branch shape*.—Young; flattened, mature; tetragonal.

*Branch color*.—Young; 145B to 145C, mature; 144A, older branches; 199B, trunk; striations of N200A and 199D.

*Branch surface*.—Young and mature stems; slightly glossy, tomentulose, older branches; slightly sheen and very slightly rugose, trunk; rugose, matte.

*Branching habit*.—Freely and multi-branching habit.

*Internode length*.—Average of 4 cm.

Foliage description:

*Leaf number*.—An average of 12 (6 pairs) per lateral branch.

*Leaf arrangement*.—Opposite.

*Leaf shape*.—Whole leaf; ovate, leaflet; lanceolate.

*Leaf size*.—Whole leaf; 10 cm in length and width, leaflet; 7 cm in length, 3 cm in width.

*Leaf division*.—Compound, palmate with 5 leaflets.

*Leaflet base*.—Cuneate.

*Leaflet apex*.—Acuminate.

*Leaflet margin*.—Serrate.

*Leaflet venation*.—Pinnate, upper and lower surface color; translucent, N144A.

*Leaflet attachment*.—Petiolate.

*Leaflet surface*.—Both surfaces soft to touch, tomentulose and matte.

*Leaf color*.—Young upper surface; 1443A, young lower surface; 138B, mature upper surface; 137A, mature lower surface; N138B.

*Petioles*.—Average of 3 cm in length and 2 mm in diameter, slightly cupped, both surfaces tomentulose, color; 138A with a thin line on the upper surface of 145B.

*Petiolules*.—Up to 5 mm in length and 1 mm in width, both surfaces tomentulose, color; 137A with a thin line on the upper surface of 145B.

Flower description:

*Inflorescence type*.—Terminal racemose-panicle.

*Inflorescence size*.—An average of 15 cm in height and 7 cm in width.

*Lastingness of inflorescence*.—Inflorescences are showy for an average of 2 weeks, individual flowers last an average of 2 days, self-cleaning.

*Inflorescence quantity*.—1 per lateral branch, 16 per plant.

*Fragrance*.—Very faint, slightly musky.

*Quantity of flowers*.—An average of 500 flowers and buds per inflorescence.

*Flower type*.—Bilabiate (one larger petal and one 4-lobed).

*Flower size*.—An average of 8 mm in width and 1.5 cm in depth.

*Flower buds*.—Obovate in shape, average of 1.5 mm in length, 1 mm in diameter, surface is glabrous, color: young buds; 139D, maturing buds before burst; 84D.

*Flower aspect*.—Upright and outward.

*Pedicel*.—Moderately strong, up to 2 mm in length and 1 mm in diameter, surface is tomentose, color; 139D.

*Peduncle*.—Strong, flexible, up to 17 cm in length and 2 mm in diameter, surface is tomentose, color; 139D.

*Petals*.—5, petals are fused into base to form the corolla tube, tube is an average of 5 mm in length and 3 mm in width, center lower petal; cupped downward, 8 mm in length, 5 mm in width, oblong shape, rounded apex, both surfaces glabrous and velvety, upper surface center edges ruffled and moderately covered with tuffs of tomentose hairs, 0.4 mm in length, N81A in color, undulate margins, other petals; slightly cupped inward, 4 mm in length, 3 mm in width, pointed shape, acute apex, both surfaces glabrous and velvety, entire margins, color of all petals: when opening and fully open upper surface; 92A, when opening and fully open lower surface; 85C and 85D, upper surface fades and diminishes to N89A, lower surface fades and diminishes to 85D.

*Calyx*.—Consists of 5 fused sepals with acute apices, an average of 4 mm in length and 3 mm in diameter.

*Sepals*.—An average of 5 in a single whorl, 1 mm in length, 0.4 mm in width, fused, elliptical in shape, entire margins, apiculate apex, both surfaces are densely flocculent, outer surface 142C, inner surface 141A.

Reproductive organs:

*Gynoecium*.—Pistil; 1, style; an average of 7 mm in length, 0.5 mm in diameter, 77A in color, stigma; forked, 0.5 mm in length, 76A in color, ovary; inferior, 141A in color and 1 mm in diameter.

*Androecium*.—Stamens; 4, 4.5 mm in length, glabrous surface, anther; dorsifixed, 1 mm in length, 0.5 mm in diameter, N92C in color, filaments; 4 mm in length, 0.5 mm in diameter, 76A in color, pollen; is moderate in quantity and 159D in color.

*Fruit and seed*.—Average of 50 per branch, drupe, oval to round in shape, surface is glossy and glabrous, average of 5 mm length and diameter, immature color; 145A, mature color; a blend of 145A and 183A, each drupe contains one seed that is about 3 mm in length and diameter, dull surface, 145C in color.

It is claimed:

1. A new and distinct cultivar of *Vitex* plant named 'Bailtexfour' as herein illustrated and described.

* * * * *